United States Patent
Ishikawa et al.

(10) Patent No.: US 11,155,526 B2
(45) Date of Patent: *Oct. 26, 2021

(54) METHOD FOR PRODUCING KAKEROMYCIN AND DERIVATIVES THEREOF

(71) Applicants: OP BIO FACTORY CO., LTD., Uruma (JP); SEED RESEARCH INSTITUTE CO., LTD., Kunigami (JP)

(72) Inventors: Teruhiko Ishikawa, Okayama (JP); Morita Iwami, Kunigami (JP)

(73) Assignees: OP BIO FACTORY CO., LTD., Uruma (JP); SEED RESEARCH INSTITUTE CO., LTD., Kunigami (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/138,374

(22) Filed: Sep. 21, 2018

(65) Prior Publication Data

US 2019/0152929 A1     May 23, 2019

Related U.S. Application Data

(62) Division of application No. 15/554,002, filed as application No. PCT/JP2016/055891 on Feb. 26, 2016, now Pat. No. 10,106,509.

(30) Foreign Application Priority Data

Feb. 27, 2015 (JP) ................................. 2015-039363

(51) Int. Cl.
| | |
|---|---|
| *C07D 211/44* | (2006.01) |
| *C07D 211/46* | (2006.01) |
| *C07D 211/74* | (2006.01) |
| *C07D 261/04* | (2006.01) |
| *C07D 498/04* | (2006.01) |
| *C07B 33/00* | (2006.01) |
| *C07C 225/06* | (2006.01) |
| *C07C 271/18* | (2006.01) |

(52) U.S. Cl.
CPC ............ *C07D 261/04* (2013.01); *C07B 33/00* (2013.01); *C07C 225/06* (2013.01); *C07C 271/18* (2013.01); *C07D 211/44* (2013.01); *C07D 211/46* (2013.01); *C07D 211/74* (2013.01); *C07D 498/04* (2013.01); *Y02P 20/55* (2015.11)

(58) Field of Classification Search
CPC ........................ C07D 211/46; C07D 211/44
See application file for complete search history.

(56) References Cited

U.S. PATENT DOCUMENTS 10,106,509 B2 * 10/2018 Ishikawa ............... C07C 271/18

OTHER PUBLICATIONS

Chemical Abstract Service STN Registry Database [online], Registry No. 1926-53-0 [Entered STN: Nov. 16, 1984]. (Year: 1984).*
Chemical Abstract Service STN Registry Database [online], Registry No. 51-35-4 [Entered STN: Nov. 16, 1984]. (Year: 1984).*
Groenhagen et al. J. Org. Chem. 2014, 10, 1421-1432. (Year: 2014).*

* cited by examiner

*Primary Examiner* — Amanda L. Aguirre
(74) *Attorney, Agent, or Firm* — Leydig, Voit & Mayer, Ltd.

(57) ABSTRACT

Provided is a production method of kakeromycin and a derivative thereof showing an antifungal activity and cytotoxicity and expected as a new antifungal agent or anticancer agent, by chemical synthesis. A production method of a compound represented by the formula (1):

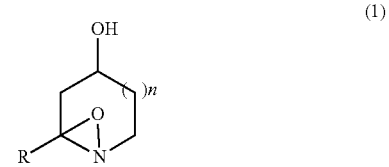

(1)

wherein R is an optionally substituted hydrocarbon group or an optionally substituted heterocyclic group; and n is 0 or 1, or a salt thereof, including a step of subjecting a compound represented by the formula (2):

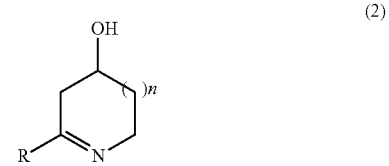

(2)

wherein R and n are as defined above, or a salt thereof, to an oxidation reaction.

9 Claims, No Drawings

METHOD FOR PRODUCING KAKEROMYCIN AND DERIVATIVES THEREOF

CROSS-REFERENCE TO RELATED APPLICATIONS

This patent application is a divisional of copending U.S. patent application Ser. No. 15/554,002, filed on Aug. 27, 2017, which the U.S. national phase of International Patent Application No. PCT/JP2016/055891, filed on Feb. 26, 2016, which claims the benefit of Japanese Patent Application No. 2015-039363, filed Feb. 27, 2015, the disclosures of which are incorporated herein by reference in their entireties for all purposes.

TECHNICAL FIELD

The present invention relates to a production method of kakeromycin and a derivative thereof.

BACKGROUND ART

In recent years, along with an increase in elderly people, progress of advanced medicine, immunodeficiency of late stage cancer patients and the like, infections with fungi have been increasing. These infections provide serious effects, often causing death. Since there are not many kinds of existing antifungal agents, and their toxicity is high, the mother nucleus of a new antifungal agent, which is different from that of conventional medicaments, has been desired. In addition, since the use of antifungal agents causes increased emergence of resistant bacteria, the development of a new medicament has been earnestly desired. While candin-based antifungal agents show low toxicity, since the molecular weight thereof is large, reactivity with serum poses problems. Azole-based antifungal agents have a problem in that administration at a high concentration is difficult in view of the toxicity thereof. Therefore, an effective, low-molecular-weight compound showing low reactivity with serum and low toxicity has been strongly desired.

Conventionally, in search of a pharmaceutical product seed compound from microbial metabolites, terrestrial separation sources have been mainly harvested and subjected to microorganism separation. The microbial metabolites found to date include penicillin and adriamycin, and a number of antibiotics and anticancer agents were found and utilized as therapeutic drugs for infection, cancer and the like. However, due to the continuous search over a long term, microbial metabolites obtained from the land areas are mostly known compounds, and a secondary metabolite to be a candidate for a novel medicament is extremely difficult to obtain. Consequently, the development of a novel medicament by natural substance drug discovery corporations was rapidly reduced. To overcome the situation, screening using a chemical library (natural substance and synthesized compound) has been conducted on a global scale. Unexpectedly, however, a promising novel medicament candidate compound was not obtained from the chemical library. Under such circumstances, it is extremely difficult to obtain a new medicament candidate compound.

In view of the aforementioned current situation in the search of a novel medicament candidate compound, the marine microorganism resources have drawing attention. Marine microorganism resources have been scarcely utilized, and have a high possibility of affording a novel secondary metabolite.

Recently, a new compound represented by the following formula:

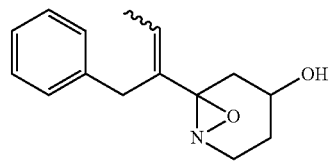

which was found from a microorganism collected from the seabed sand around the Kakeroma island of Kagoshima Prefecture, Amami Islands, was named "Kakeromycin". The "kakeromycin" shows an antifungal activity, particularly, a strong antibacterial activity against pathogens of candidiasis, highly possibly shows a new antibacterial action different from those of existing antifungal agents, and further research and development in the future is expected. In addition, since the "kakeromycin" shows cytotoxicity to HepG2 liver cancer cell and PANC-1 pancreas cancer cell, its development as an anticancer agent is expected.

SUMMARY OF THE INVENTION

Problems to be Solved by the Invention

An object of the present invention is to provide a method of producing kakeromycin and a derivative thereof by chemical synthesis.

Means of Solving the Problems

The present inventors have conducted intensive studies in an attempt to solve the above-mentioned problem and found a method of producing kakeromycin and a derivative thereof represented by the following formula (1) by chemical synthesis, which resulted in the completion of the present invention.

Therefore, the present invention provides the following.
[1] A method of producing a compound represented by the formula (1):

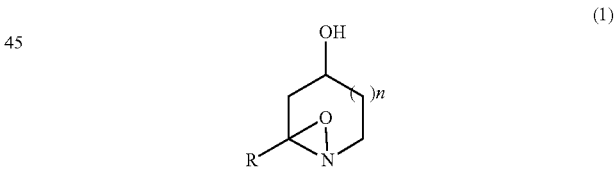

wherein
R is an optionally substituted hydrocarbon group or an optionally substituted heterocyclic group; and
n is 0 or 1,
or a salt thereof, which comprises a step of subjecting a compound represented by the formula (2):

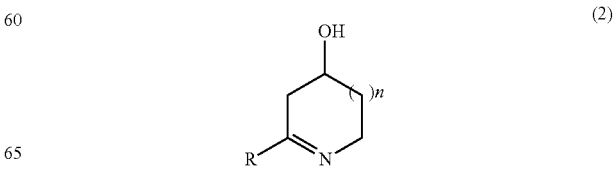

wherein R and n are as defined above,
or a salt thereof to an oxidation reaction;
[2] the production method of [1], further comprising a step of producing a compound represented by the formula (2) or a salt thereof by subjecting a compound represented by the formula (3):

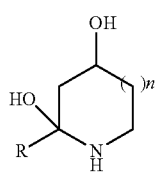

(3)

wherein R and n are as defined in [1],
or a salt thereof, to an intramolecular dehydration condensation reaction;
[3] the production method of [2], further comprising a step of producing a compound represented by the formula (3) or a salt thereof by subjecting a compound represented by the formula (4):

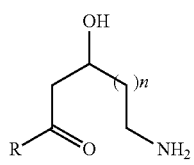

(4)

wherein R and n are as defined in [1],
or a salt thereof, to an intramolecular addition reaction;
[4] the production method of [3], further comprising a step of producing a compound represented by the formula (4) or a salt thereof by subjecting an acyl protecting group of an amino group of a compound represented by the formula (5):

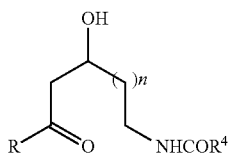

(5)

wherein $R^4$ is an optionally substituted hydrocarbon group or an optionally substituted hydrocarbon-oxy group, and R and n are as defined in [1],
or a salt thereof, to a deprotection reaction;
[5] the production method of [4], further comprising a step of producing a compound represented by the formula (5) or a salt thereof by subjecting a compound represented by the formula (6):

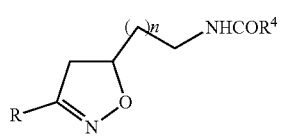

(6)

wherein R and n are as defined in [1], and $R^4$ is as defined in [4],
or a salt thereof, to a reduction reaction;
[6] the production method of [5], further comprising a step of producing a compound represented by the formula (6) or a salt thereof by subjecting a compound represented by the formula (7):

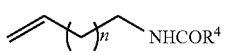

(7)

wherein n is as defined in [1], and $R^4$ is as defined in [4], or a salt thereof, and a compound represented by the formula (8):

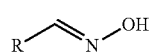

(8)

wherein R is as defined in [1],
or a salt thereof, to a cyclization addition reaction;
[7] the production method of any one of [1]-[6], further comprising a step of producing a compound represented by the formula (1-1):

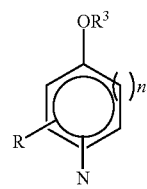

(1-1)

wherein $R^3$ is an optionally substituted hydrocarbon group or an optionally substituted acyl group, and R and n are as defined in [1],
or a salt thereof, by subjecting a hydroxyl group of a compound represented by the formula (1) or a salt thereof to a protection reaction;
[8] the production method of any one of [1]-[7], wherein R is a group represented by the formula (A):

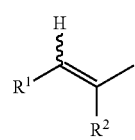

(A)

wherein $R^1$ and $R^2$ are the same or different and each is an optionally substituted hydrocarbon group or an optionally substituted heterocyclic group;
[9] the production method of any one of [1]-[8], wherein n is 1;

[10] a compound represented by the formula (1):

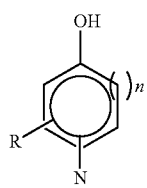

(1)

wherein
R is an optionally substituted hydrocarbon group or an optionally substituted heterocyclic group; and
n is 0 or 1,
or a salt thereof;
[11] the compound of [10], wherein R is a group represented by the formula (A):

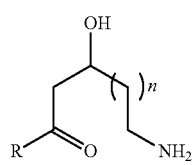

(A)

wherein $R^1$ and $R^2$ are the same or different and each is an optionally substituted hydrocarbon group or an optionally substituted heterocyclic group,
or a salt thereof;
[12] a compound represented by the formula (2):

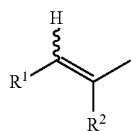

(2)

wherein
R is an optionally substituted hydrocarbon group or an optionally substituted heterocyclic group; and
n is 0 or 1,
or a salt thereof;
[13] a compound represented by the formula (3):

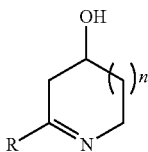

(3)

wherein
R is an optionally substituted hydrocarbon group or an optionally substituted heterocyclic group; and
n is 0 or 1,
or a salt thereof;

[14] a compound represented by the formula (4):

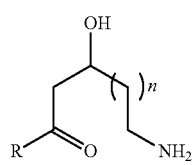

(4)

wherein
R is an optionally substituted hydrocarbon group or an optionally substituted heterocyclic group; and
n is 0 or 1,
or a salt thereof;
[15] a compound represented by the formula (5):

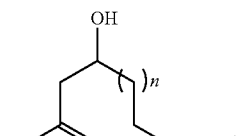

(5)

wherein
R is an optionally substituted hydrocarbon group or an optionally substituted heterocyclic group;
$R^4$ is an optionally substituted hydrocarbon group or an optionally substituted hydrocarbon-oxy group; and
n is 0 or 1,
or a salt thereof;
[16] a compound represented by the formula (6):

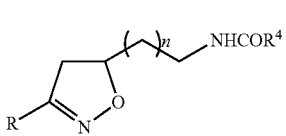

(6)

wherein
R is an optionally substituted hydrocarbon group or an optionally substituted heterocyclic group;
$R^4$ is an optionally substituted hydrocarbon group or an optionally substituted hydrocarbon-oxy group; and
n is 0 or 1,
or a salt thereof.

Effect of the Invention

According to the production method of the present invention, kakeromycin and a derivative thereof which show an antifungal activity and cytotoxicity, and are expected as new antifungal agents and anticancer agents can be produced by chemical synthesis.

DESCRIPTION OF EMBODIMENTS

The definition of each group used in the structural formulas in the present specification is described in detail below.
R, $R^1$ and $R^2$ are each an optionally substituted hydrocarbon group or an optionally substituted heterocyclic group.
$R^3$ is an optionally substituted hydrocarbon group or an optionally substituted acyl group.

$R^4$ is an optionally substituted hydrocarbon group or an optionally substituted hydrocarbon-oxy group.

Examples of the "hydrocarbon group" of the "optionally substituted hydrocarbon group" and the "hydrocarbon-" (hydrocarbon moiety) of the "optionally substituted hydrocarbon-oxy group" include $C_{1-20}$ alkyl group, $C_{2-20}$ alkenyl group, $C_{2-20}$ alkynyl group, $C_{3-20}$ cycloalkyl group, $C_{3-20}$ cycloalkenyl group, $C_{6-20}$ aryl group, and $C_{7-20}$ aralkyl group.

Examples of the "$C_{1-20}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, and 2-ethylbutyl.

Examples of the "$C_{2-20}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, and 5-hexenyl.

Examples of the "$C_{2-20}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, and 4-methyl-2-pentynyl.

Examples of the "$C_{3-20}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, and adamantyl.

Examples of the "$C_{3-20}$ cycloalkenyl group" include cyclopropenyl, cyclobutenyl, cyclopentenyl, cyclohexenyl, cycloheptenyl, and cyclooctenyl.

Examples of the "$C_{6-20}$ aryl group" include phenyl, 1-naphthyl, 2-naphthyl, 1-anthryl, 2-anthryl, and 9-anthryl.

Examples of the "$C_{7-20}$ aralkyl group" include benzyl, phenethyl, naphthylmethyl, and phenylpropyl.

Examples of the "heterocyclic group" of the "optionally substituted heterocyclic group" include (i) aromatic heterocyclic group, (ii) nonaromatic heterocyclic group and (iii) 7- to 10-membered crosslinked heterocyclic group, each containing, as a ring-constituting atom besides carbon atom, 1 to 4 hetero atoms selected from nitrogen atom, sulfur atom and oxygen atom.

Examples of the "aromatic heterocyclic group" include a 5- to 14-membered (preferably 5- to 10-membered) aromatic heterocyclic group containing, as a ring-constituting atom besides carbon atom, 1 to 4 hetero atoms selected from nitrogen atom, sulfur atom and oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered condensed polycyclic (preferably di- or tricyclic) aromatic heterocyclic groups such as benzothiophenyl, benzofuranyl, benzimidazolyl, benzoxazolyl, benzoisooxazolyl, benzothiazolyl, benzoisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acrydinyl, phenazinyl, phenothiazinyl, phenoxazinyl and the like.

Examples of the "nonaromatic heterocyclic group" include a 3- to 14-membered (preferably 4- to 10-membered) nonaromatic heterocyclic group containing, as a ring-constituting atom besides carbon atom, 1 to 4 hetero atoms selected from nitrogen atom, sulfur atom and oxygen atom.

Preferable examples of the "nonaromatic heterocyclic group" include 3- to 8-membered monocyclic nonaromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered condensed polycyclic (preferably di- or tricyclic) nonaromatic heterocyclic groups such as dihydrobenzofuranyl, dihydrobenzoimidazolyl, dihydrobenzooxazolyl, dihydrobenzothiazolyl, dihydrobenzoisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzoazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

Preferable examples of the "7- to 10-membered crosslinked heterocyclic group" include quinuclidinyl, and 7-azabicyclo[2.2.1]heptanyl.

Examples of the "acyl group" of the "optionally substituted acyl group" include formyl group, carboxy group, $C_{1-6}$ alkyl-carbonyl group, $C_{2-6}$ alkenyl-carbonyl group, $C_{3-10}$ cycloalkyl-carbonyl group, $C_{3-10}$ cycloalkenyl-carbonyl group, $C_{6-14}$ aryl-carbonyl group, $C_{7-16}$ aralkyl-carbonyl group, aromatic heterocyclyl-carbonyl group, non-aromatic heterocyclyl-carbonyl group, $C_{1-6}$ alkoxy-carbonyl group, $C_{6-14}$ aryloxy-carbonyl group, $C_{7-16}$ aralkyloxy-carbonyl group, and carbamoyl group.

Examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl, and heptanoyl.

Examples of the "$C_{2-6}$ alkenyl-carbonyl group" include ethenylcarbonyl, 1-propenylcarbonyl, 2-propenylcarbonyl, 2-methyl-1-propenylcarbonyl, 1-butenylcarbonyl, 2-butenylcarbonyl, 3-butenylcarbonyl, 3-methyl-2-butenylcarbonyl, 1-pentenylcarbonyl, 2-pentenylcarbonyl, 3-pentenylcarbonyl, 4-pentenylcarbonyl, 4-methyl-3-pentenylcarbonyl, 1-hexenylcarbonyl, 3-hexenylcarbonyl, and 5-hexenylcarbonyl.

Examples of the "$C_{3-20}$ cycloalkyl-carbonyl group" include cyclopropylcarbonyl, cyclobutylcarbonyl, cyclopentylcarbonyl, cyclohexylcarbonyl, cycloheptylcarbonyl, cyclooctylcarbonyl, bicyclo[2.2.1]heptylcarbonyl, bicyclo[2.2.2]octylcarbonyl, bicyclo[3.2.1]octylcarbonyl, and adamantylcarbonyl.

Examples of the "$C_{3-20}$ cycloalkenyl-carbonyl group" include cyclopropenylcarbonyl, cyclobutenylcarbonyl, cyclopentenylcarbonyl, cyclohexenylcarbonyl, cycloheptenylcarbonyl, and cyclooctenylcarbonyl.

Examples of the "$C_{6-14}$ aryl-carbonyl group" include benzoyl, 1-naphthoyl, and 2-naphthoyl.

Examples of the "$C_{7-16}$ aralkyl-carbonyl group" include phenylacetyl, and phenylpropionyl.

Examples of the "aromatic heterocyclyl-carbonyl group" include nicotinoyl, isonicotinoyl, thenoyl, and furoyl.

Examples of the "non-aromatic heterocyclyl-carbonyl group" include morpholinylcarbonyl, piperidinylcarbonyl, and pyrrolidinylcarbonyl.

Examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, and hexyloxycarbonyl.

Examples of the "$C_{6-14}$ aryloxy-carbonyl group" include phenyloxycarbonyl, 1-naphthyloxycarbonyl, and 2-naphthyloxycarbonyl.

Examples of the "$C_{7-16}$ aralkyloxy-carbonyl group" include benzyloxycarbonyl, and phenethyloxycarbonyl.

Examples of the "substituent" of the "optionally substituted hydrocarbon group", "optionally substituted hydrocarbon-oxy group", "optionally substituted heterocyclic group" and "optionally substituted acyl group" include the following:
(1) halogen atom,
(2) nitro group,
(3) cyano group,
(4) oxo group,
(5) hydroxy group,
(6) optionally substituted $C_{1-6}$ alkoxy group,
(7) optionally substituted $C_{6-14}$ aryloxy group,
(8) optionally substituted $C_{7-16}$ aralkyloxy group,
(9) optionally substituted aromatic heterocyclyl-oxy group,
(10) optionally substituted non-aromatic heterocyclyl-oxy group,
(11) optionally substituted $C_{1-6}$ alkyl-carbonyloxy group,
(12) optionally substituted $C_{6-14}$ aryl-carbonyloxy group,
(13) optionally substituted $C_{1-6}$ alkoxy-carbonyloxy group,
(14) optionally substituted mono- or di-$C_{1-6}$ alkyl-carbamoyloxy group,
(15) optionally substituted $C_{6-14}$ aryl-carbamoyloxy group,
(16) optionally substituted 5- to 14-membered aromatic heterocyclyl-carbonyloxy group,
(17) optionally substituted 3- to 14-membered non-aromatic heterocyclyl-carbonyloxy group,
(18) optionally substituted $C_{1-6}$ alkylsulfonyloxy group,
(19) optionally substituted $C_{6-14}$ arylsulfonyloxy group,
(20) optionally substituted $C_{1-6}$ alkylthio group,
(21) optionally substituted 5- to 14-membered aromatic heterocyclic group,
(22) optionally substituted 3- to 14-membered nonaromatic heterocyclic group,
(23) formyl group,
(24) carboxy group,
(25) optionally substituted $C_{1-6}$ alkyl-carbonyl group,
(26) optionally substituted $C_{6-14}$ aryl-carbonyl group,
(27) optionally substituted 5- to 14-membered aromatic heterocyclyl-carbonyl group,
(28) optionally substituted 3- to 14-membered non-aromatic heterocyclyl-carbonyl group,
(29) optionally substituted $C_{1-6}$ alkoxy-carbonyl group,
(30) optionally substituted $C_{6-14}$ aryloxy-carbonyl group,
(31) optionally substituted $C_{7-16}$ aralkyloxy-carbonyl group,
(32) carbamoyl group,
(33) thiocarbamoyl group,
(34) optionally substituted mono- or di-$C_{1-6}$ alkyl-carbamoyl group,
(35) optionally substituted $C_{6-14}$ aryl-carbamoyl group,
(36) optionally substituted 5- to 14-membered aromatic heterocyclyl-carbamoyl group,
(37) optionally substituted 3- to 14-membered non-aromatic heterocyclyl-carbamoyl group,
(38) optionally substituted $C_{1-6}$ alkylsulfonyl group,
(39) optionally substituted $C_{6-14}$ arylsulfonyl group,
(40) optionally substituted 5- to 14-membered aromatic heterocyclyl-sulfonyl group,
(41) optionally substituted $C_{1-6}$ alkylsulfinyl group,
(42) optionally substituted $C_{6-14}$ arylsulfinyl group,
(43) optionally substituted 5- to 14-membered aromatic heterocyclyl-sulfinyl group,
(44) amino group,
(45) optionally substituted mono- or di-$C_{1-6}$ alkylamino group,
(46) optionally substituted mono- or di-$C_{6-14}$ arylamino group,
(47) optionally substituted 5- to 14-membered aromatic heterocyclyl-amino group,
(48) optionally substituted $C_{7-16}$ aralkylamino group,
(49) formylamino group,
(50) optionally substituted $C_{1-6}$ alkyl-carbonylamino group,
(51) optionally substituted ($C_{1-6}$ alkyl) ($C_{1-6}$ alkyl-carbonyl) amino group,
(52) optionally substituted $C_{6-14}$ aryl-carbonylamino group,
(53) optionally substituted $C_{1-6}$ alkoxy-carbonylamino group,
(54) optionally substituted $C_{7-16}$ aralkyloxy-carbonylamino group,
(55) optionally substituted $C_{1-6}$ alkylsulfonylamino group,
(56) optionally substituted $C_{6-14}$ arylsulfonylamino group,
(57) optionally substituted $C_{1-6}$ alkyl group,
(58) optionally substituted $C_{2-6}$ alkenyl group,
(59) optionally substituted $C_{2-6}$ alkynyl group,
(60) optionally substituted $C_{3-10}$ cycloalkyl group,
(61) optionally substituted $C_{3-10}$ cycloalkenyl group, and
(62) optionally substituted $C_{6-14}$ aryl group.

The number of the above-mentioned "substituent" of the "optionally substituted hydrocarbon group", "optionally substituted hydrocarbon-oxy group", "optionally substituted heterocyclic group" and "optionally substituted acyl group" is, for example, 1 to 5, preferably 1 to 3. When the number of the substituents is two or more, the respective substituents may be the same or different.

R is preferably an optionally substituted $C_{2-20}$ alkenyl group (e.g., ethenyl), more preferably, a group represented by the formula (A):

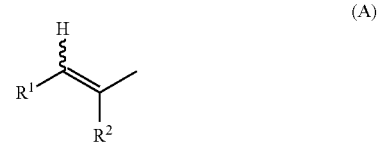

(A)

wherein $R^1$ and $R^2$ are the same or different and each is an optionally substituted hydrocarbon group or an optionally substituted heterocyclic group, more preferably, a group represented by the formula (A) wherein $R^1$ and $R^2$ are the same or different and each is an optionally substituted $C_{1-20}$ alkyl group (e.g., methyl) or an optionally substituted $C_{7-20}$ aralkyl group (e.g., benzyl), particularly preferably, a group represented by the formula (A) wherein $R^1$ and $R^2$ are the same or different and each is a $C_{1-20}$ alkyl group (e.g., methyl) or a $C_{7-20}$ aralkyl group (e.g., benzyl).

In another embodiment of the present invention, R is preferably an optionally substituted $C_{2-20}$ alkenyl group (e.g., ethenyl), an optionally substituted $C_{1-20}$ alkyl group (e.g., heptyl), an optionally substituted $C_{6-20}$ aryl group (e.g., phenyl, naphthyl) or an optionally substituted $C_{7-20}$ aralkyl group (e.g., phenylethyl), more preferably, a group represented by the formula (A):

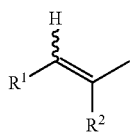

(A)

wherein $R^1$ and $R^2$ are the same or different and each is an optionally substituted hydrocarbon group or an optionally substituted heterocyclic group, an optionally substituted $C_{1-20}$ alkyl group (e.g., heptyl), an optionally substituted $C_{6-20}$ aryl group (e.g., phenyl, naphthyl) or an optionally substituted $C_{7-20}$ aralkyl group (e.g., phenylethyl), more preferably, a group represented by the formula (A) wherein $R^1$ and $R^2$ are the same or different and each is an optionally substituted $C_{1-20}$ alkyl group (e.g., methyl), an optionally substituted $C_{6-20}$ aryl group (e.g., phenyl) or an optionally substituted $C_{7-20}$ aralkyl group (e.g., benzyl, phenylethyl), an optionally substituted $C_{1-20}$ alkyl group (e.g., heptyl), an optionally substituted $C_{6-20}$ aryl group (e.g., phenyl, naphthyl) or an optionally substituted $C_{7-20}$ aralkyl group (e.g., phenylethyl), particularly preferably, a group represented by the formula (A) wherein $R^1$ and $R^2$ are the same or different and each is a $C_{1-20}$ alkyl group (e.g., methyl), a $C_{6-20}$ aryl group (e.g., phenyl) optionally substituted by a halogen atom (e.g., chlorine atom) or $C_{7-20}$ aralkyl group (e.g., benzyl, phenylethyl), a $C_{1-20}$ alkyl group (e.g., heptyl), a $C_{6-20}$ aryl group (e.g., phenyl, naphthyl) or a $C_{7-20}$ aralkyl group (e.g., phenylethyl).

$R^3$ is preferably an optionally substituted $C_{1-20}$ alkyl group (e.g., methyl) or an optionally substituted $C_{1-6}$ alkyl-carbonyl group (e.g., acetyl), more preferably, a $C_{1-20}$ alkyl group (e.g., methyl) or a $C_{1-6}$ alkyl-carbonyl group (e.g., acetyl), further preferably, methyl or acetyl.

$R^4$ is preferably an optionally substituted $C_{1-20}$ alkyl group (e.g., methyl), an optionally substituted $C_{6-20}$ aryl group (e.g., phenyl), an optionally substituted $C_{1-20}$ alkyl-oxy group (e.g., tert-butyloxy) or an optionally substituted $C_{7-20}$ aralkyl-oxy group (e.g., benzyloxy), more preferably a $C_{1-20}$ alkyl group (e.g., methyl), a $C_{6-20}$ aryl group (e.g., phenyl), a $C_{1-20}$ alkyl-oxy group (e.g., tert-butyloxy) or a $C_{7-20}$ aralkyl-oxy group (e.g., benzyloxy), further preferably, methyl, phenyl, tert-butyloxy or benzyloxy, particularly preferably tert-butyloxy.

n is 0 or 1. n is preferably 1.

The production method of the present invention is explained below.

The whole scheme of the production method of the present invention is shown below.

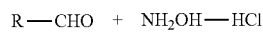

9

Step 1

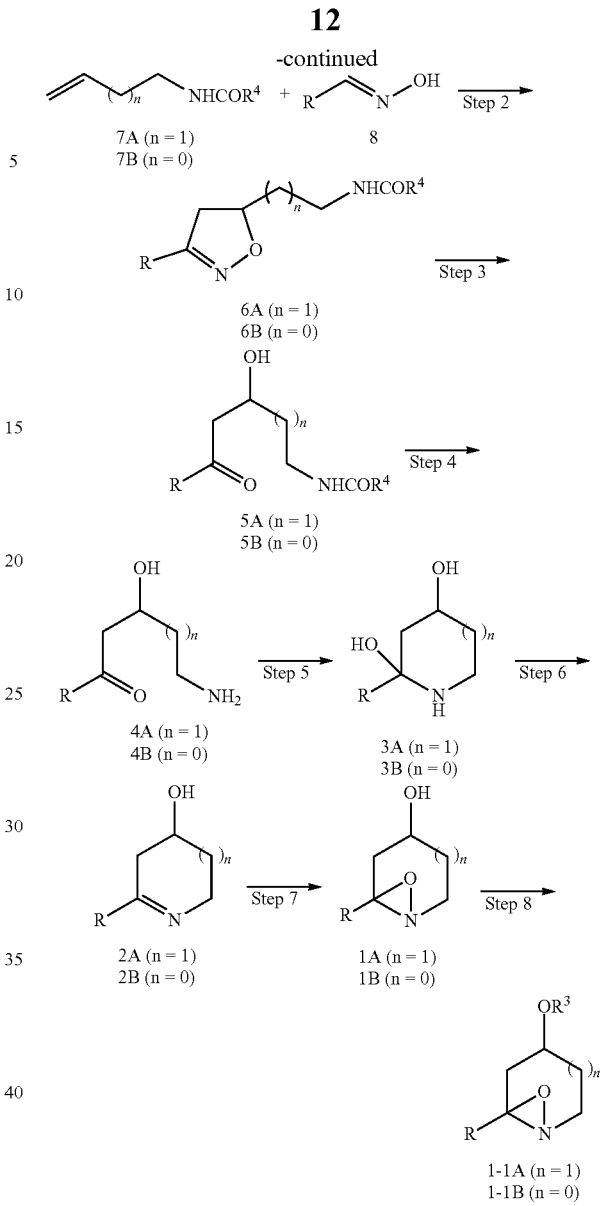

wherein each symbol is as defined above.

(Step 1: Production of Oxime 8)

Oxime (8) can be synthesized by a dehydration condensation reaction of aldehyde (9) and hydroxylamine prepared from hydroxylamine hydrochloride and a base. As the base, sodium hydrogen carbonate, potassium hydrogen carbonate, sodium carbonate, potassium carbonate, tertiary amines such as triethylamine and the like, and the like can be used at generally 1-5 molar equivalents, preferably 1-1.5 molar equivalents, relative to hydroxylamine hydrochloride, and sodium hydrogen carbonate is particularly preferable. Hydroxylamine hydrochloride can be used at generally 1-5 molar equivalents, preferably 1-1.5 molar equivalents, relative to aldehyde (9). The reaction temperature is generally 0-50° C., preferably 20-30° C. While the reaction time varies depending on the kind of the reagents, reaction temperature and the like, it is generally 1-48 hr, preferably 2-10 hr. As the reaction solvent, THF, water, acetonitrile, ethyl acetate, dichloromethane, or a mixed solvent thereof and the like can be used, and a mixed solvent of THF-water is particularly preferable.

Aldehyde (9) may be a commercially available product, and can also be produced according to a method known per se or a method analogous thereto.

(Step 2: Production of Dihydroisoxazole 6A, 6B)

Dihydroisoxazole (6A, 6B) can be synthesized by (3+2) cyclization addition reaction of nitrile oxide prepared from oxime (8) and aqueous sodium hypochlorite solution, or oxime (8) and chloramine-T, and N-acylaminobutene (7A) or N-acylaminopropene (7B). The aqueous sodium hypochlorite solution, or chloramine-T, can be used at generally 1-5 molar equivalents, preferably 1-2 molar equivalents, relative to oxime 8. Oxime (8) can be used at generally 0.5-3 molar equivalents, preferably 0.8-1.2 molar equivalents, relative to N-acylaminobutene (7A) or N-acylaminopropene (7B). The reaction temperature is generally 0-80° C., preferably 20-30° C. While the reaction time varies depending on the kind of the reagents, reaction temperature and the like, it is generally 1-48 hr, preferably 2-10 hr. As the reaction solvent, THF, ethyl acetate, dichloromethane, ethanol, methanol, acetonitrile or a mixed solvent thereof and the like can be used.

N-acylaminobutene (7A) or N-acylaminopropene (7B) may be a commercially available product, and can also be produced according to a method known per se or a method analogous thereto.

(Step 3: Production of N-acylaminohydroxyketone 5A, 5B)

N-acylaminohydroxyketone (5A, 5B) can be synthesized by reducing N—O bond of dihydroisoxazole (6A, 6B). As the reducing agent, molybdenum hexacarbonyl, cobalt octacarbonyl, iron, zinc, magnesium and the like can be used at generally 1-5 molar equivalents, preferably 1-2 molar equivalents, relative to dihydroisoxazole (6A, 6B), though subject to change depending on the kind of the reagents, reaction temperature and the like, and molybdenum hexacarbonyl is particularly preferable. The reaction temperature is generally 0-100° C., preferably 70-90° C. While the reaction time varies depending on the kind of the reagents, reaction temperature and the like, it is generally 1-24 hr, preferably 1-3 hr. As the reaction solvent, acetonitrile, propionitrile, water, THF, ethyl acetate, dichloromethane, dichloroethane, or a mixed solvent thereof and the like can be used, and a mixed solvent of acetonitrile-water is particularly preferable.

(Step 4: Production of aminohydroxyketone 4A, 4B)

Aminohydroxyketone (4A, 4B) can be synthesized by removing an acyl protecting group of the amino group of N-acylaminohydroxyketone (5A, 5B). As the deprotecting agent, trifluoroacetic acid, hydrochloric acid, sodium hydroxide, potassium hydroxide and the like can be used at generally 1-50 molar equivalents, preferably 1-10 molar equivalents, relative to N-acylaminohydroxyketone (5A, 5B), and trifluoroacetic acid is particularly preferable. The reaction temperature is generally 0-50° C., preferably 20-30° C. While the reaction time varies depending on the kind of the reagents, reaction temperature and the like, it is generally 1-24 hr, preferably 1-3 hr. As the reaction solvent, THF, ethyl acetate, dichloromethane, dichloroethane, or a mixed solvent thereof and the like can be used, and particularly, dichloromethane and dichloroethane are preferable.

(Step 5: Production of Cyclic Hemiaminal 3A, 3B)

Cyclic hemiaminal (3A, 3B) can be synthesized by an intramolecular addition reaction of aminohydroxyketone (4A, 4B). While an intramolecular addition reaction sometimes proceeds without particularly using a reaction agent, when an acid catalyst is necessary, trifluoroacetic acid, acetic acid, p-toluenesulfonic acid, methanesulfonic acid and the like, can be used at generally 0.01-5 molar equivalents, preferably 0.01-1 equimolar amount, relative to aminohydroxyketone (4A, 4B). The reaction temperature is generally 0-100° C., preferably 30-50° C. While the reaction time varies depending on the kind of the reagents, reaction temperature and the like, it is generally 1-24 hr, preferably 1-6 hr. As the reaction solvent, THF, ethyl acetate, dichloromethane, dichloroethane, toluene, or a mixed solvent thereof and the like can be used, and THF or dichloroethane is particularly preferable.

(Step 6: Production of Cyclic Imine 2A, 2B)

Cyclic imine (2A, 2B) can be synthesized by an intramolecular dehydration condensation reaction of cyclic hemiaminal (3A, 3B). As the dehydrating agent, trifluoroacetic acid, acetic acid, molecular sieve, anhydrous sodium sulfate and the like can be used at generally 0.01-100 molar equivalents, preferably 0.01-10 molar equivalents, relative to cyclic hemiaminal (3A, 3B), though subject to change depending on the kind of the reagents, reaction temperature and the like. The reaction temperature is generally 0-100° C., preferably 20-60° C. While the reaction time varies depending on the kind of the reagents, reaction temperature and the like, it is generally 1-24 hr, preferably 3-12 hr. As the reaction solvent, THF, ethyl acetate, dichloromethane, dichloroethane, toluene, or a mixed solvent thereof and the like can be used, and THF is particularly preferable.

(Step 7: Production of Bicyclic Oxaziridine 1A, 1B)

Bicyclic oxaziridine (1A, 1B) can be synthesized by an oxidation reaction of cyclic imine (2A, 2B). As the oxidant, m-chloroperbenzoic acid, peracetic acid and the like can be used at generally 1-5 molar equivalents, preferably 1-2 molar equivalents, relative to cyclic imine (2A, 2B), and m-chloroperbenzoic acid is particularly preferable. The reaction temperature is generally 0-50° C., preferably 10-30° C. While the reaction time varies depending on the kind of the reagents, reaction temperature and the like, it is generally 0.5-12 hr, preferably 1-2 hr. As the reaction solvent, THF, ethyl acetate, dichloromethane, dichloroethane, toluene, ethanol, methanol, acetonitrile, or a mixed solvent thereof and the like can be used, and THF and dichloromethane are particularly preferable.

(Step 8: Production of Bicyclic Oxaziridine Derivative 1-1A, 1-1B)

The bicyclic oxaziridine derivative (1-1A, 1-1B) can be synthesized by protecting the hydroxyl group of bicyclic oxaziridine (1A, 1B).

When $R^3$ is an optionally substituted hydrocarbon group, the protection reaction can be performed using the corresponding halide as a protector and a base each at generally 1-10 molar equivalents, preferably 1-3 molar equivalents, relative to the bicyclic oxaziridine derivative (1-1A, 1-1B). As the halide, methyl iodide is particularly preferable. As the base, sodium carbonate, potassium carbonate, sodium hydride, n-butyllithium and the like can be used, and sodium hydride is particularly preferable. The reaction temperature is generally 0-50° C., preferably 20-30° C. While the reaction time varies depending on the kind of the reagents, reaction temperature and the like, it is generally 0.5-24 hr, preferably 1-12 hr. As the reaction solvent, THF, dimethyl sulfoxide, dimethylformamide, acetonitrile, dichloromethane, dichloroethane, or a mixed solvent thereof and the like can be used, and dimethyl sulfoxide or acetonitrile is particularly preferable.

When $R^3$ is an optionally substituted acyl group, the protection reaction can be performed using the corresponding halogenated acyl compound or acid anhydride as a protector at generally 1-10 molar equivalents, preferably 1-3 molar equivalents, relative to the bicyclic oxaziridine derivative (1-1A, 1-1B) in the presence of an amine base. As the halogenated acyl compound or acid anhydride, acetic anhydride is particularly preferable. As the amine base, a tertiary amine such as triethylamine, diisopropylethylamine and the like, or a pyridine derivative such as pyridine, dimethylaminopyridine and the like can be used at generally 1-10 molar equivalents, preferably 1-3 molar equivalents, relative to the bicyclic oxaziridine derivative (1-1A, 1-1B), and triethylamine or dimethylaminopyridine is particularly preferable. The reaction temperature is generally 0-50° C., preferably 20-30° C. While the reaction time varies depending on the kind of the reagents, reaction temperature and the like, it is generally 0.5-24 hr, preferably 1-12 hr. As the reaction solvent, THF, ethyl acetate, acetonitrile, dichloromethane, dichloroethane, or a mixed solvent thereof and the like can be used, and THF or dichloromethane is particularly preferable.

The kakeromycin derivatives represented by the formulas (1) and (1-1) (excluding kakeromycin) obtained by the production method of the present invention, as well as synthetic intermediates thereof represented by the formulas (2), (3), (4), (5) and (6) are novel compounds.

The kakeromycin and a derivative thereof (bicyclic oxaziridine and a derivative thereof) and a synthetic intermediate thereof obtained by the production method of the present invention may be salts. Examples of such salt include salts with inorganic acids such as hydrochloric acid, hydrobromic acid, nitric acid, sulfuric acid, phosphoric acid and the like, and salts with organic acids such as acetic acid, phthalic acid, fumaric acid, oxalic acid, tartaric acid, maleic acid, citric acid, succinic acid, methanesulfonic acid, p-toluenesulfonic acid and the like. Of these salts, a pharmaceutically acceptable salt is preferable.

The kakeromycin and a derivative thereof (bicyclic oxaziridine and a derivative thereof) obtained by the production method of the present invention have a strong antifungal activity against a broad range of fungi, and are expected to be new antifungal agents. In addition, the kakeromycin and a derivative thereof show cytotoxicity against cancer cells. Therefore, a compound containing the kakeromycin or a derivative thereof as an active ingredient can be used as a medicament, a pesticide and the like.

Examples of the fungi to be the target of the antifungal agent include, but are not limited to, fungi such as the genus *Candida* (e.g., *Candida albicans, Candida parapsilosis, Candida tropicalis, Candida krusei, Candida glabrata, Candida quilliermondii, Candida lusitaniae* etc.), the genus *Aspergillus* (e.g., *Aspergillus fumigatus, Aspergillus flavus, Aspergillus niger, Aspergillus terreus* etc.), the genus *Trichophyton* (e.g., *Trichophyton rubrum, Trichophyton mentagrophytes, Trichophyton tonsurans, Microsporum canis, Microsporum gypseum, Trichophyton verrucosum* etc.) and the like. Mycosis is not particularly limited, and deep skin mycosis, deep mycosis, mycetoma, and fungemia can be mentioned.

When the antifungal agent is used as a pesticide, the target crop is not particularly limited and, for example, plants such as grain (e.g., rice, barley, wheat, rye, oats, corn, kaoliang etc.), beans (soybean, adzuki bean, broad bean, pea, peanut etc.), fruit-tree, fruits (apple, citrus, pear, grapes, peach, ume (Japanese plum), cherry, walnut, almond, banana, strawberry etc.), vegetables (cabbage, tomato, spinach, broccoli, lettuce, onion, green onion, bell pepper etc.), root vegetables (carrot, potato, sweet potato, radish, lotus root, turnip etc.), crops for processing (cotton, hemp, kozo (paper mulberry), mitsumata plant, rape seed, beet, hop, sugarcane, sugar beet, olive, rubber, coffee, tobacco, tea etc.), gourds (pumpkin, cucumber, watermelon, melon etc.), grasses (orchard grass, sorghum, timothy, clover, alfalfa etc.), sods (Korean lawn grass, bentgrass etc.), crops for flavor etc. (lavender, rosemary, thyme, parsley, pepper, ginger etc.), flowering plants (*chrysanthemum*, rose, orchid etc.) and the like can be mentioned. The antifungal agent can be used for controlling the diseases related to the aforementioned fungi in the crops, by treating the target crop and/or seed of the target crop with an effective amount thereof.

The pesticide can be used at the following form, and generally used together with an adjuvant conventionally used in the pharmaceutical fields. The kakeromycin and a derivative thereof obtained by the production method of the present invention are formulated by a known method into, for example, emulsion stock solution, sprayable paste, sprayable or dilutable solution, dilutable emulsion, wettable agent, water soluble powder, powder, granule, flowable pesticide, dry flowable pesticide, smoking agent, fumigant and, for example, capsule made of a polymer substance.

As additive and carrier when the object is a solid agent, plant-derived powder such as soy flour, wheat flour and the like, mineral fine powder such as diatomaceous earth, apatite, plaster, talc, bentonite, clay and the like, and organic and inorganic compounds such as sodium benzoate, urea, salt cake and the like can be used.

When a liquid dosage form is desired, vegetable oil, mineral oil, kerosene, aromatic hydrocarbons such as xylene and toluene, amides such as formamide, and dimethylformamide, sulfoxides such as dimethyl sulfoxide, ketones such as methyl isobutyl ketone and acetone, trichloroethylene, water and the like are used as solvents. To afford these preparations in a uniform and stable form, a surfactant can also be added where necessary. The thus-obtained wettable agent, emulsion, aqueous solution, flowable pesticide, and dry flowable pesticide are diluted with water to a given concentration and used as a suspension or emulsion, and powder and granule are used by directly spraying on the soil or plant.

The content and dose of the active ingredient in a pesticide containing the kakeromycin or a derivative thereof obtained by the production method of the present invention can be changed in a wide range depending on the dosage form, the kind of fungi to be the application target, target crop and the like.

On the other hand, when the antifungal agent is used as a medicament, it can be administered to a treatment target, for example, a mammal (e.g., human, mouse, rat, hamster, rabbit, cat, dog, bovine, sheep, monkey etc.) by an oral or parenteral administration route (e.g., intravenous injection, intramuscular injection, subcutaneous administration, rectal administration, transdermal administration).

When the antifungal agent is transdermally administered, it can contain, besides the above-mentioned active ingredient, oily base, emulsifier and emulsion stabilizer, solubilizing agents, powder component, polymer component, adhesiveness improver, film-forming agent, pH adjuster, antioxidant, antiseptic agent, preservative, shape retention agent, moisturizer, skin protector, algefacient, flavor, colorant, chelating agent, lubricant, blood circulation promoter, astringent, tissue repair promoter, adiaphoretic, plant extraction component, animal extraction component, anti-inflammatory agent, antipruritic agent and the like as necessary. As these additives, those generally used for preparations can be used.

The antifungal agent can be used by formulating the above-mentioned components other than the active ingredient and the like into external drugs such as cream, liquid, lotion, emulsion, tincture, ointment, aqueous gel, oily gel, aerosol, powder, shampoo, soap, enamel agent for application to nail and the like, by a method conventionally used in the field of pharmaceutical preparations.

When the antifungal agent is orally administered, it can be prepared into a dosage form suitable for oral administration such as capsule, tablet, granule, powder, pill, fine granules, troche and the like. These preparations can be produced using additives generally used for oral preparations, such as excipient, filler, binder, moistening agent, disintegrant, surfactant, lubricant, dispersing agent, buffering agent, preservative, solubilizing agent, antiseptic agent, flavoring agent, soothing agent, stabilizer and the like by a conventional method.

Examples of the cells to be the target of the anticancer agent include, but are not limited to, cancer cells such as HepG2 cell (liver cancer cell), PANC1 cell (pancreas cancer cell) and the like. The cancer is not particularly limited, and brain tumor, skin cancer, leukemia, esophagus cancer, gastric cancer, colorectal cancer, breast cancer, prostate cancer, rectal cancer, osteosarcoma and the like can be mentioned.

EXAMPLES

The present invention is explained in more detail by referring to the following Examples. These do not limit the present invention, and may be changed within the scope of the present invention.

$^1$H and $^{13}$C NMR spectra were measured by a nuclear magnetic resonance apparatus (manufactured by Varian, 400 MR and Mercury-300), and all δ values are shown in ppm. Mass spectrum was measured by HPLC-Chip/QTOF mass spectrometry system (Agilent Technologies), and m/z values are shown.

Example 1

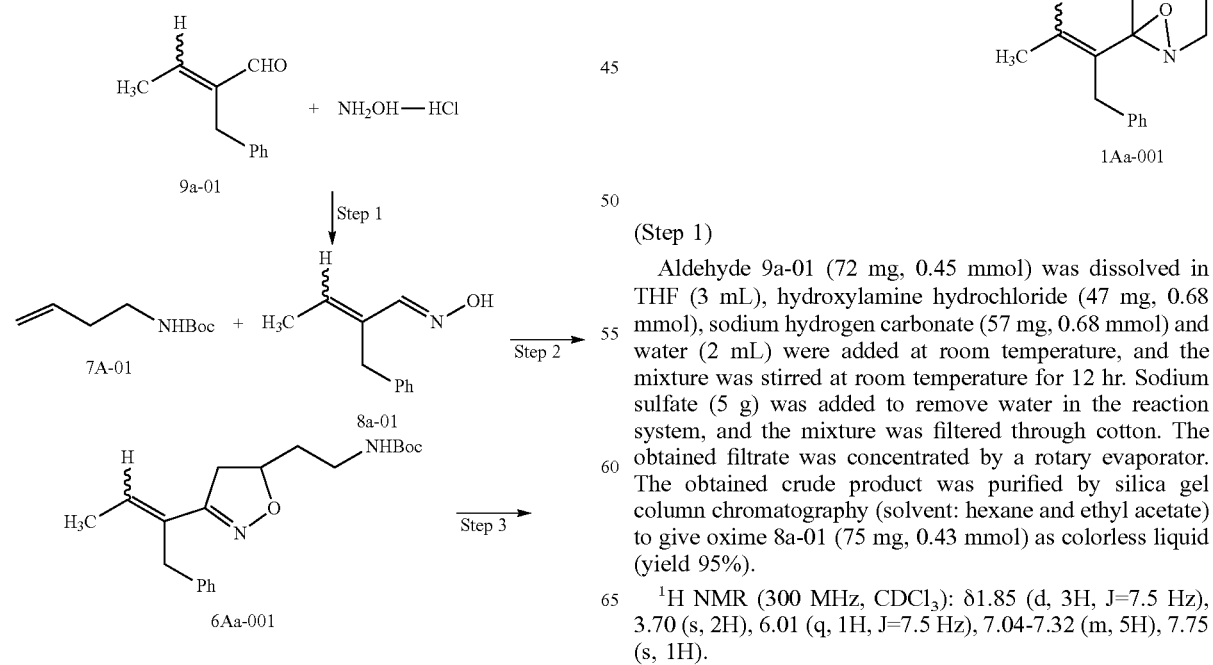

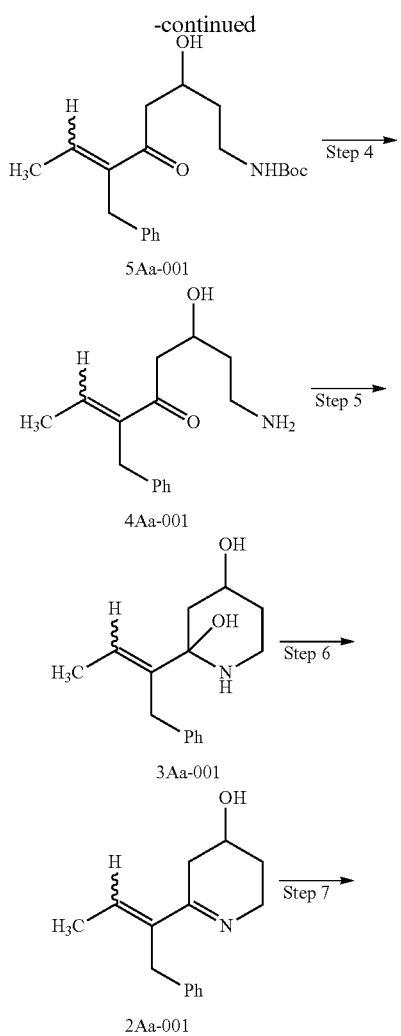

(Step 1)

Aldehyde 9a-01 (72 mg, 0.45 mmol) was dissolved in THF (3 mL), hydroxylamine hydrochloride (47 mg, 0.68 mmol), sodium hydrogen carbonate (57 mg, 0.68 mmol) and water (2 mL) were added at room temperature, and the mixture was stirred at room temperature for 12 hr. Sodium sulfate (5 g) was added to remove water in the reaction system, and the mixture was filtered through cotton. The obtained filtrate was concentrated by a rotary evaporator. The obtained crude product was purified by silica gel column chromatography (solvent: hexane and ethyl acetate) to give oxime 8a-01 (75 mg, 0.43 mmol) as colorless liquid (yield 95%).

$^1$H NMR (300 MHz, CDCl$_3$): δ1.85 (d, 3H, J=7.5 Hz), 3.70 (s, 2H), 6.01 (q, 1H, J=7.5 Hz), 7.04-7.32 (m, 5H), 7.75 (s, 1H).

(Step 2)

Oxime 8a-01 (52 mg, 0.30 mmol) and N-Boc-aminobutene 7A-01 (62 mg, 0.36 mmol)) were dissolved in THF (5 mL), aqueous sodium hypochlorite solution (5%, 2 mL) was added at 0° C., and the mixture was stirred at room temperature for 12 hr. Sodium sulfate (5 g) was added to remove water in the reaction system, and the mixture was filtered through cotton. The obtained filtrate was concentrated by a rotary evaporator. The obtained crude product was purified by silica gel column chromatography (solvent: hexane and ethyl acetate) to give dihydroisoxazole 6Aa-001 (120 mg, 0.35 mmol) as colorless liquid (yield 86%). $^1$H NMR (300 MHz, CDCl$_3$): δ1.41 (s, 9H), 1.72-1.86 (m, 2H), 1.87 (d, 3H, J=7.5 Hz), 2.75 (dd, 1H, J=8.1, 16.2 Hz), 3.18 (dd, 1H, J=10.2, 16.2 Hz), 3.15-3.30 (m, 2H), 3.80 (s, 2H), 4.55-4.68 (m, 1H), 4.68-4.98 (br, 1H), 5.95 (q, 1H, J=7.5 Hz), 7.05-7.28 (m, 5H).

$^{13}$C NMR (75 MHz, CDCl$_3$): δ14.4, 28.3, 32.6, 35.2, 37.6, 39.8, 79.1, 79.6, 125.8, 128.2, 128.4, 131.5, 131.7, 139.6, 156.0, 158.8.

(Step 3)

Dihydroisoxazole 6Aa-001 (110 mg, 0.32 mmol) and molybdenum hexacarbonyl (170 mg, 0.64 mmol) were dissolved in acetonitrile (3 mL), water (0.5 mL) was added, and the mixture was stirred at 85° C. for 2 hr. Ethyl acetate (5 mL) was added, and the mixture was stirred at room temperature for 24 hr. The obtained mixture was filtered through celite by using ethyl acetate, and the filtrate was concentrated by a rotary evaporator. The obtained crude product was purified by silica gel column chromatography (solvent: hexane and ethyl acetate) to give N-Boc aminohydroxyketone 5Aa-001 (83 mg, 0.24 mmol) as colorless liquid (yield 75%).

$^1$H NMR (300 MHz, CDCl$_3$): δ1.20-1.62 (m, 2H), 1.43 (s, 9H), 1.96 (d, 3H, J=7.5 Hz), 2.78-2.83 (m, 2H), 3.10-3.41 (m, 2H), 3.68 (s, 2H), 4.16-4.28 (m, 1H), 4.75-5.10 (br, 1H), 6.94 (q, 1H, J=7.5 Hz), 7.08-7.24 (m, 5H).

(Steps 4 and 5)

N-Boc aminohydroxyketone 5Aa-001 (50 mg, 0.14 mmol) was dissolved in dichloroethane (3 mL), trifluoroacetic acid (0.5 mL) was added, and the mixture was stirred at room temperature for 1 hr. The reaction mixture was concentrated by a rotary evaporator to give a mixture (31 mg, 0.13 mol) of aminohydroxyketone 4Aa-001 and cyclic hemiaminal 3Aa-001 as yellow liquid (yield 87%).

$^1$H NMR (300 MHz, CDCl$_3$): δ1.20-1.64 (m, 2H), 1.95 (d, 3H, J=7.5 Hz), 2.76-2.96 (m, 4H), 3.67 (s, 2H), 4.12-4.28 (m, 1H), 6.92 (q, 1H, J=7.5 Hz), 7.08-7.24 (m, 5H).

(Step 6)

A mixture (30 mg, 0.12 mmol) of aminohydroxyketone 4Aa-001 and cyclic hemiaminal 3Aa-001 was dissolved in THF (3 mL), 4A-molecular sieve (100 mg) was added, and the mixture was stirred at room temperature for 12 hr. The reaction mixture was filtered through celite by using ethyl acetate as a solvent, and concentrated by a rotary evaporator to give cyclic imine 2Aa-001 (24 mg, 0.10 mmol) as yellow liquid (yield 83%).

(Step 7)

Cyclic imine 2Aa-001 (9 mg, 0.039 mmol) was dissolved in THF (3 mL), m-chloroperbenzoic acid (11 mg) was added, and the mixture was stirred at room temperature for 3 hr and concentrated by a rotary evaporator. The obtained crude product was purified by silica gel column chromatography (solvent: hexane and ethyl acetate) to give bicyclic oxaziridine 1Aa-001 (3 mg, 0.012 mmol) as yellow liquid (yield 31%).

$^1$H NMR (400 MHz, CDCl$_3$): δ1.16-1.36 (m, 1H), 1.69 (d, 3H, J=7.6 Hz), 1.80-1.98 (m, 1H), 1.99 (dd, 1H, J=6.9, 15.1 Hz), 2.35 (ddd, 1H, J=1.3, 6.2, 15.1 Hz), 3.15-3.25 (m, 1H), 3.36-3.60 (m, 3H), 3.75-3.84 (m, 1H), 5.91 (q, 1H, J=6.9 Hz), 7.05-7.28 (m, 5H).

MS: m/z 246 ([M+1], C$_{15}$H$_{19}$NO$_2$)

Example 2

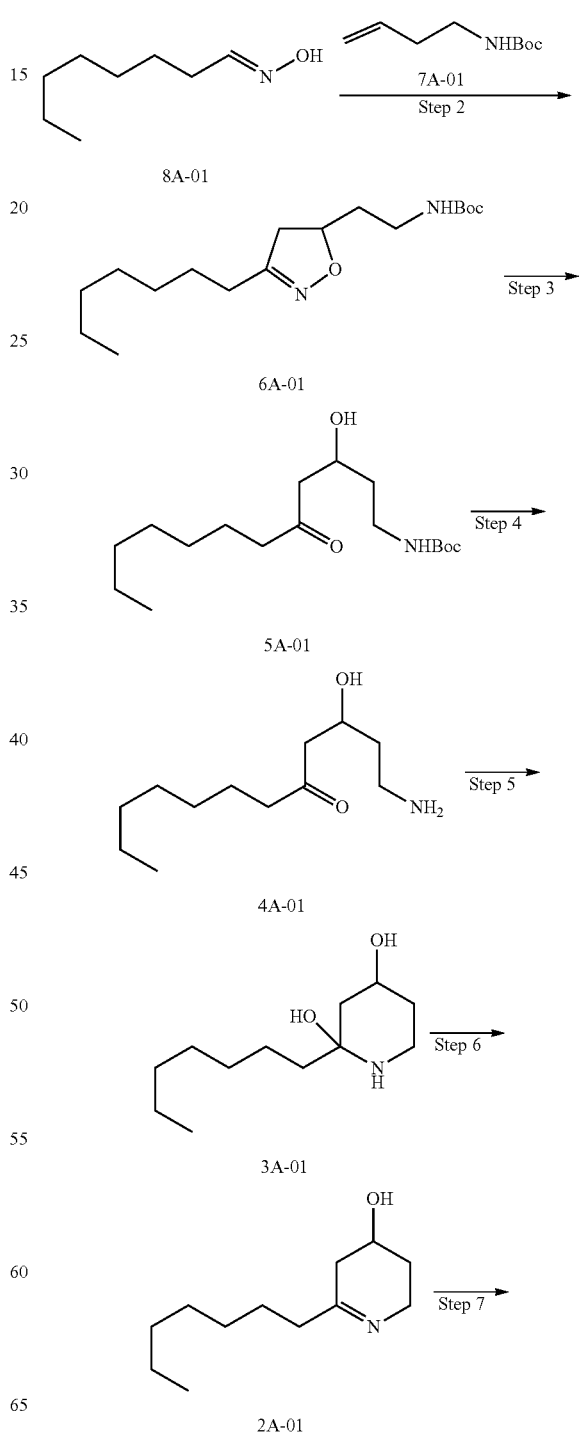

-continued

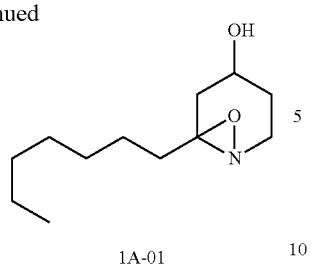

1A-01

(Step 2)

In the same manner as in Example 1, Step 2, and by using octylaldehyde oxime 8A-01 and N-Boc-aminobutene 7A-01 as substrates, dihydroisoxazole 6A-01 was obtained as colorless liquid (yield 75%).

$^1$H NMR (300 MHz, CDCl$_3$): δ0.82 (t, 3H, J=7.5 Hz), 1.16-1.80 (m, 12H), 1.39 (s, 9H), 2.20-2.36 (m, 2H), 2.56 (dd, 1H, J=8.1, 16.2 Hz), 2.98 (dd, 1H, J=10.2, 16.2 Hz), 3.10-3.24 (m, 2H), 4.48-4.60 (m, 1H), 4.92-5.00 (br, 1H).

(Step 3)

In the same manner as in Example 1, Step 3, and by using dihydroisoxazole 6A-01 as a substrate, N-Boc aminohydroxyketone 5A-01 was obtained as colorless liquid (yield 69%).

$^1$H NMR (300 MHz, CDCl$_3$): δ0.83 (t, 3H, J=7.5 Hz), 1.16-1.76 (m, 10H), 1.40 (s, 9H), 2.32-2.60 (m, 6H), 3.16-3.44 (m, 2H), 4.00-4.26 (m, 1H), 4.96-5.04 (br, 1H).

(Steps 4 and 5)

In the same manner as in Example 1, Steps 4 and 5, and by using N-Boc aminohydroxyketone 5A-01 as a substrate, a mixture of aminohydroxyketone 4A-01 and cyclic hemiaminal 3A-01 was obtained as yellow liquid (yield 90%).

$^1$H NMR (300 MHz, CDCl$_3$): δ0.83 (t, 3H, J=7.5 Hz), 1.16-1.76 (m, 10H), 2.32-2.60 (m, 6H), 2.64-3.02 (m, 2H), 3.98-4.16 (m, 1H).

(Steps 6 and 7)

In the same manner as in Example 1, Step 6, and by using as a substrate, a mixture of aminohydroxyketone 4A-01 and cyclic hemiaminal 3A-01, cyclic imine 2A-01 was obtained. In the same manner as in Example 1, Step 7, bicyclic oxaziridine 1A-01 was obtained as yellow liquid (yield 23%).

$^1$H NMR (300 MHz, CDCl$_3$): δ0.83 (t, 3H, J=7.5 Hz), 1.20-1.74 (m, 10H), 1.92-2.20 (m, 2H), 2.32-2.60 (m, 4H), 3.78-4.12 (m, 2H), 4.12-4.22 (m, 1H).

MS: m/z 214 ([M+1], C$_{12}$H$_{23}$NO$_2$)

Example 3

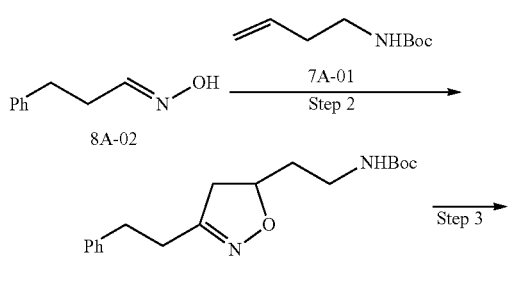

-continued

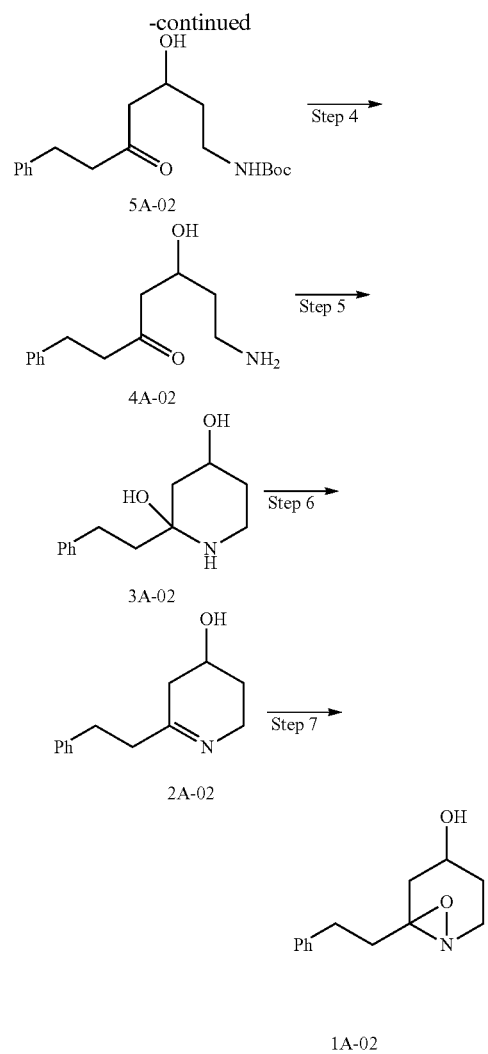

(Step 2)

In the same manner as in Example 1, Step 2, and by using 3-phenylpropionaldehyde oxime 8A-02 and N-Boc-aminobutene 7A-01 as substrates, dihydroisoxazole 6A-02 was obtained as colorless liquid (yield 77%).

$^1$H NMR (300 MHz, CDCl$_3$): δ1.43 (s, 9H), 1.62-1.80 (m, 2H), 2.40-2.66 (m, 2H), 2.82-3.02 (m, 4H), 3.16-3.24 (m, 2H), 4.50-4.62 (m, 1H), 4.85-4.98 (br, 1H), 7.14-7.48 (m, 5H).

(Step 3)

In the same manner as in Example 1, Step 3, and by using dihydroisoxazole 6A-02 as a substrate, N-Boc aminohydroxyketone 5A-02 was obtained as colorless liquid (yield 69%).

$^1$H NMR (300 MHz, CDCl$_3$): δ1.41 (s, 9H), 1.60-1.80 (m, 2H), 2.46-2.62 (m, 2H), 2.64-2.94 (m, 4H), 3.04-3.42 (m, 2H), 4.02-4.18 (m, 1H), 4.98-5.04 (br, 1H), 7.14-7.32 (m, 5H).

(Steps 4 and 5)

In the same manner as in Steps 4 and 5 of Example 1, and by using N-Boc aminohydroxyketone 5A-02 as a substrate, a mixture of aminohydroxyketone 4A-02 and cyclic hemiaminal 3A-02 was obtained as yellow liquid (yield 92%).

$^1$H NMR (300 MHz, CDCl$_3$): δ1.42 (s, 9H), 1.60-1.80 (m, 2H), 2.46-2.62 (m, 2H), 2.62-3.20 (m, 6H), 4.00-4.18 (m, 1H), 7.12-7.34 (m, 5H).

(Steps 6 and 7)

In the same manner as in Example 1, Step 6, and by using a mixture of aminohydroxyketone 4A-02 and cyclic hemiaminal 3A-02 as a substrate, cyclic imine 2A-02 was obtained. In the same manner as in Example 1, Step 7, bicyclic oxaziridine 1A-02 was obtained as yellow liquid (yield 23%).

$^1$H NMR (300 MHz, CDCl$_3$): δ1.58-1.98 (m, 6H), 2.46-2.54 (m, 2H), 3.86-4.20 (m, 2H), 4.14-4.24 (m, 1H), 7.22-7.40 (m, 5H).

MS: m/z 220 ([M+1], C$_{13}$H$_{17}$NO$_2$)

Example 4

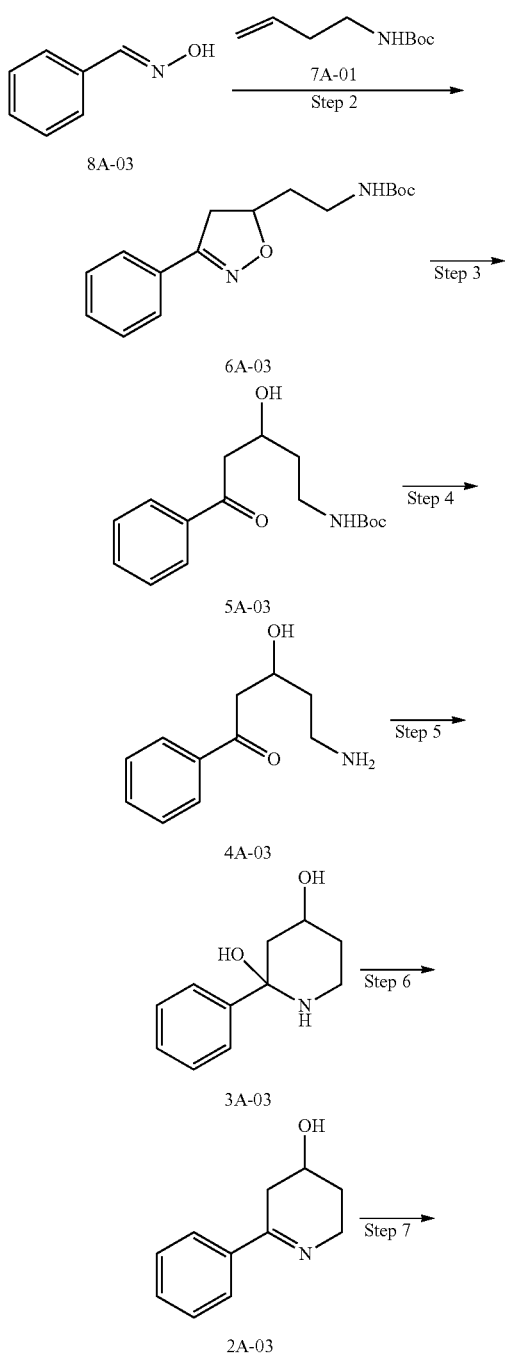

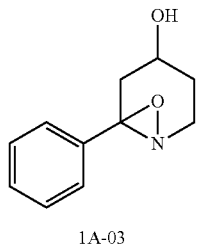

1A-03

(Step 2)

In the same manner as in Example 1, Step 2, and by using benzaldehyde oxime 8A-03 and N-Boc-aminobutene 7A-01 as substrates, dihydroisoxazole 6A-03 was obtained as colorless liquid (yield 72%).

$^1$H NMR (300 MHz, CDCl$_3$): δ1.18-1.64 (m, 2H), 1.43 (s, 9H), 2.78-2.83 (m, 2H), 3.08-3.42 (m, 2H), 4.14-4.28 (m, 1H), 4.75-5.10 (br, 1H), 7.20-7.52 (m, 5H).

(Step 3)

In the same manner as in Example 1, Step 3, and by using dihydroisoxazole 6A-03 as a substrate, N-Boc aminohydroxyketone 5A-03 was obtained as colorless liquid (yield 67%).

$^1$H NMR (300 MHz, CDCl$_3$): δ1.18-1.64 (m, 2H), 1.44 (s, 9H), 2.76-2.84 (m, 2H), 3.08-3.42 (m, 2H), 4.15-4.29 (m, 1H), 4.72-5.12 (br, 1H), 7.20-7.52 (m, 5H).

(Steps 4 and 5)

In the same manner as in Example 1, Steps 4 and 5, and by using N-Boc aminohydroxyketone 5A-03 as a substrate, a mixture of aminohydroxyketone 4A-03 and cyclic hemiaminal 3A-03 was obtained as yellow liquid (yield 90%).

$^1$H NMR (300 MHz, CDCl$_3$): δ1.16-1.66 (m, 2H), 2.74-2.84 (m, 2H), 2.62-2.98 (m, 2H), 4.14-4.28 (m, 1H), 7.20-7.52 (m, 5H).

(Steps 6 and 7)

In the same manner as in Example 1, Step 6, and by using a mixture of aminohydroxyketone 4A-03 and cyclic hemiaminal 3A-03 as a substrate, cyclic imine 2A-03 was obtained. In the same manner as in Example 1, Step 7, bicyclic oxaziridine 1A-03 was obtained as yellow liquid (yield 25%).

$^1$H NMR (300 MHz, CDCl$_3$): δ1.40-1.52 (m, 1H), 1.82-1.98 (m, 1H), 2.30-2.48 (m, 1H), 2.78-2.86 (m, 1H), 3.48-3.84 (m, 2H), 4.14-4.22 (m, 1H), 7.25-7.50 (m, 5H).

Example 5

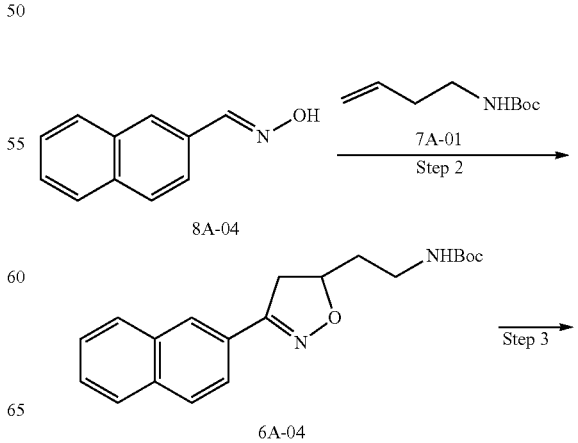

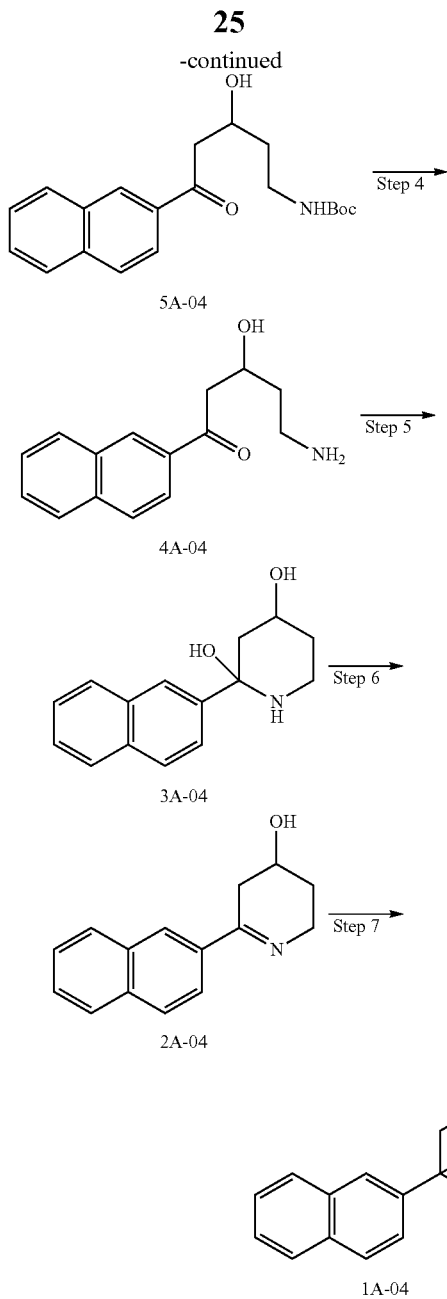

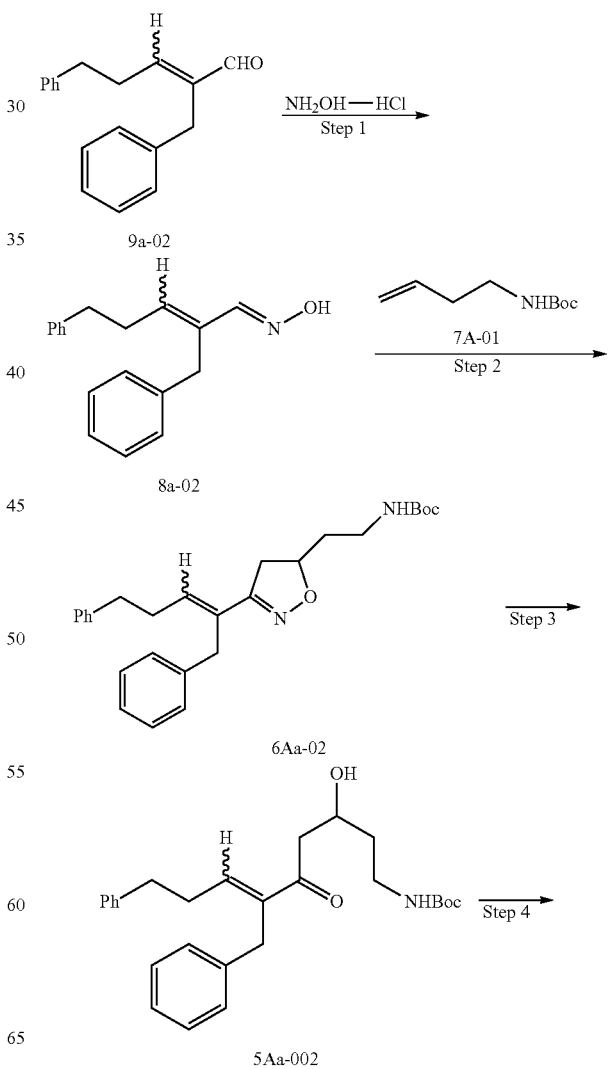

(Step 2)

In the same manner as in Example 1, Step 2, and by using 2-naphthylaldehyde oxime 8A-04 and N-Boc-aminobutene 7A-01 as substrates, dihydroisoxazole 6A-04 was obtained as colorless liquid (yield 73%).

$^1$H NMR (300 MHz, CDCl$_3$): δ1.45 (s, 9H), 1.84-2.00 (m, 2H), 3.02-3.20 (m, 1H), 3.28-3.40 (m, 2H), 3.50-3.62 (m, 1H), 4.78-4.88 (m, 1H), 4.90-5.18 (br, 1H), 7.42-8.00 (m, 7H).

(Step 3)

In the same manner as in Example 1, Step 3, and by using dihydroisoxazole 6A-04 as a substrate, N-Boc aminohydroxyketone 5A-04 was obtained as colorless liquid (yield 62%). $^1$H NMR (300 MHz, CDCl$_3$): δ1.43 (s, 9H), 1.62-1.84 (m, 2H), 3.18-3.52 (m, 4H), 4.30-4.42 (m, 1H), 5.02-5.18 (br, 1H), 7.42-8.02 (m, 6H), 8.40 (s, 1H).

(Steps 4 and 5)

In the same manner as in Example 1, Steps 4 and 5, and by using N-Boc aminohydroxyketone 5A-04 as a substrate, a mixture of aminohydroxyketone 4A-04 and cyclic hemiaminal 3A-04 was obtained as yellow liquid (yield 91%).

$^1$H NMR (300 MHz, CDCl$_3$): δ1.60-1.86 (m, 2H), 2.76-3.50 (m, 4H), 4.28-4.40 (m, 1H), 7.40-8.02 (m, 6H), 8.42 (s, 1H).

(Steps 6 and 7)

In the same manner as in Example 1, Step 6, and by using a mixture of aminohydroxyketone 4A-04 and cyclic hemiaminal 3A-04 as a substrate, cyclic imine 2A-04 was obtained. In the same manner as in Example 1, Step 7, bicyclic oxaziridine 1A-04 was obtained as yellow liquid (yield 24%).

$^1$H NMR (300 MHz, CDCl$_3$): δ1.42-1.82 (m, 2H), 1.96-2.26 (m, 2H), 3.46-3.86 (m, 2H), 4.13-4.21 (m, 1H), 7.10-8.20 (m, 7H).

MS: m/z 242 ([M+1], C$_{15}$H$_{15}$NO$_2$)

Example 6

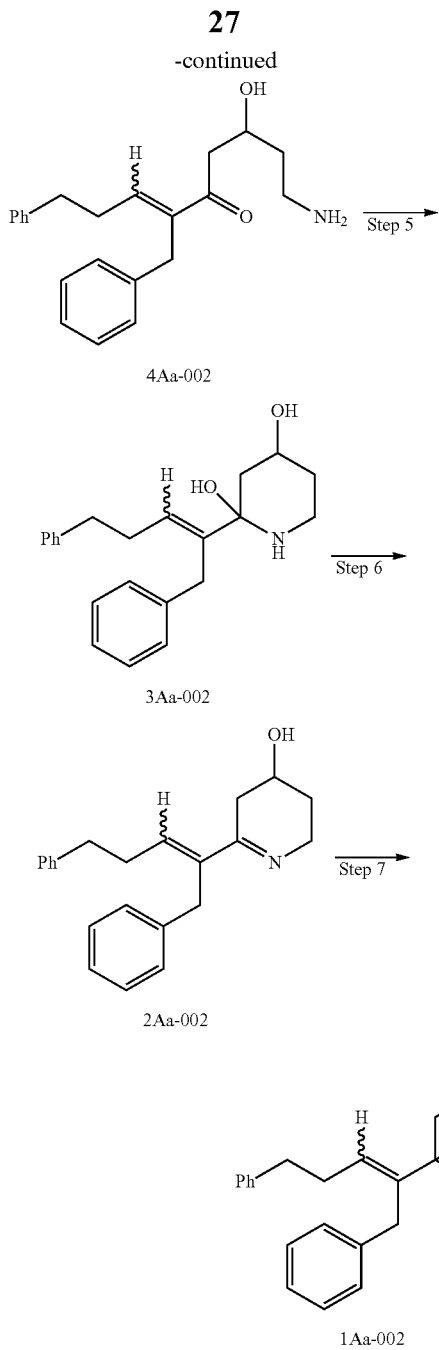

3Aa-002

2Aa-002

1Aa-002

(Step 1)

In the same manner as in Example 1, Step 1, and by using aldehyde 9a-02 and hydroxylamine hydrochloride as substrates, oxime 8a-02 was obtained as a colorless solid (yield 90%).

(Step 2)

In the same manner as in Example 1, Step 2, and by using oxime 8a-02 and N-Boc-aminobutene 7A-01 as substrates, dihydroisoxazole 6Aa-02 was obtained as colorless liquid (yield 71%).

$^1$H NMR (300 MHz, CDCl$_3$): δ1.47 (s, 9H), 2.40-2.84 (m, 7H), 3.12-3.40 (m, 3H), 3.80 (s, 2H), 4.60-4.74 (m, 1H), 4.76-5.00 (br, 1H), 5.92 (t, 1H, J=6.6 Hz), 7.16-7.40 (m, 10H).

(Step 3)

In the same manner as in Example 1, Step 3, and by using dihydroisoxazole 6Aa-02 as a substrate, N-Boc aminohydroxyketone 5Aa-002 was obtained as colorless liquid (yield 62%).

$^1$H NMR (300 MHz, CDCl$_3$): δ1.43 (s, 9H), 2.56-2.82 (m, 7H), 3.02-3.44 (m, 3H), 3.82 (s, 2H), 4.02-4.16 (m, 1H), 4.92-5.02 (br, 1H), 6.81 (t, 1H, J=6.6 Hz), 7.10-7.38 (m, 10H).

(Steps 4 and 5)

In the same manner as in Example 1, Steps 4 and 5, and by using N-Boc aminohydroxyketone 5Aa-002 as a substrate, a mixture of aminohydroxyketone 4Aa-002 and cyclic hemiaminal 3Aa-002 was obtained as yellow liquid (yield 92%).

$^1$H NMR (300 MHz, CDCl$_3$): δ2.56-2.82 (m, 7H), 2.94-3.40 (m, 3H), 3.81 (s, 2H), 43.98-4.10 (m, 1H), 6.78 (t, 1H, J=6.6 Hz), 7.10-7.40 (m, 10H).

(Steps 6 and 7)

In the same manner as in Example 1, Step 6, and by using a mixture of aminohydroxyketone 4Aa-002 and cyclic hemiaminal 3Aa-002 as a substrate, cyclic imine 2Aa-002 was obtained. In the same manner as in Example 1, Step 7, bicyclic oxaziridine 1Aa-002 was obtained as yellow liquid (yield 22%).

MS: In/Z 336 ([M+1], C$_{22}$H$_{25}$NO$_2$)

Example 7

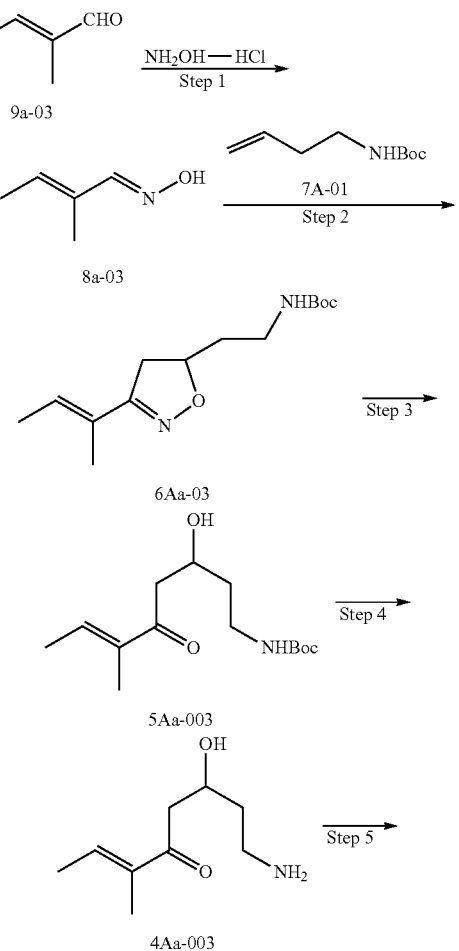

6Aa-03

5Aa-003

4Aa-003

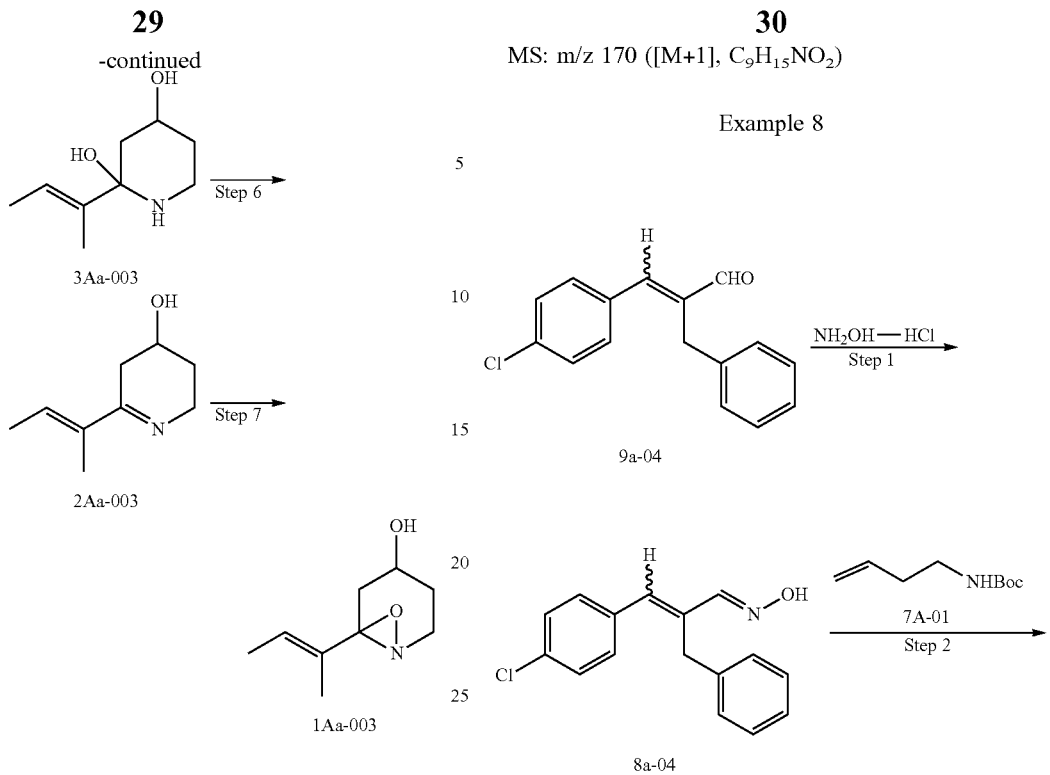

3Aa-003

2Aa-003

1Aa-003

(Step 1)
In the same manner as in Example 1, Step 1, and by using aldehyde 9a-03 and hydroxylamine hydrochloride as substrates, oxime 8a-03 was obtained as a colorless solid (yield 85%).

(Step 2)
In the same manner as in Example 1, Step 2, and by using oxime 8a-03 and N-Boc-aminobutene 7A-01 as substrates, dihydroisoxazole 6Aa-03 was obtained as colorless liquid (yield 72%).
$^1$H NMR (300 MHz, CDCl$_3$): δ1.42 (s, 9H), 1.70-1.84 (m, 2H), 1.76 (d, 3H, J=6.6 Hz), 1.92 (s, 3H), 2.64-2.80 (m, 1H), 3.22-3.35 (m, 3H), 4.58-4.64 (m, 1H), 4.80-4.98 (br, 1H), 5.72-5.82 (m, 1H).

(Step 3)
In the same manner as in Example 1, Step 2, and by using dihydroisoxazole 6Aa-03 as a substrate, N-Boc aminohydroxyketone 5Aa-003 was obtained as colorless liquid (yield 66%).
$^1$H NMR (300 MHz, CDCl$_3$): δ1.42 (s, 9H), 1.50-1.70 (m, 2H), 1.76 (s, 3H), 1.84 (d, 3H, J=6.6 Hz), 2.72-2.82 (m, 2H), 3.10-3.42 (m, 2H), 4.12-4.20 (m, 1H), 4.96-5.10 (br, 1H), 6.70-6.82 (m, 1H).

(Steps 4 and 5)
In the same manner as in Example 1, Steps 4 and 5, and by using N-Boc aminohydroxyketone 5Aa-003 as a substrate, a mixture of aminohydroxyketone 4Aa-003 and cyclic hemiaminal 3Aa-003 was obtained as yellow liquid (yield 82%).
$^1$H NMR (300 MHz, CDCl$_3$): δ1.48-1.72 (m, 2H), 1.76 (s, 3H), 1.84 (d, 3H, J=6.6 Hz), 2.72-2.82 (m, 2H), 2.96-3.22 (m, 2H), 4.02-4.12 (m, 1H), 6.68-6.82 (m, 1H).

(Steps 6 and 7)
In the same manner as in Example 1, Step 6, and by using a mixture of aminohydroxyketone 4Aa-003 and cyclic hemiaminal 3Aa-003 as a substrate, cyclic imine 2Aa-003 was obtained. In the same manner as in Example 1, Step 7, bicyclic oxaziridine 1Aa-003 was obtained as yellow liquid (yield 18%).

MS: m/z 170 ([M+1], C$_9$H$_{15}$NO$_2$)

Example 8

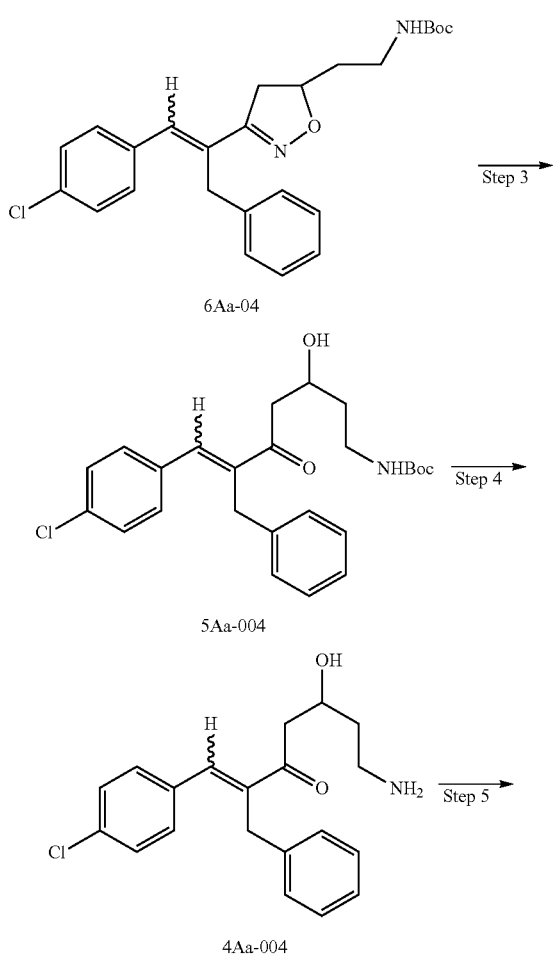

9a-04

8a-04

6Aa-04

5Aa-004

4Aa-004

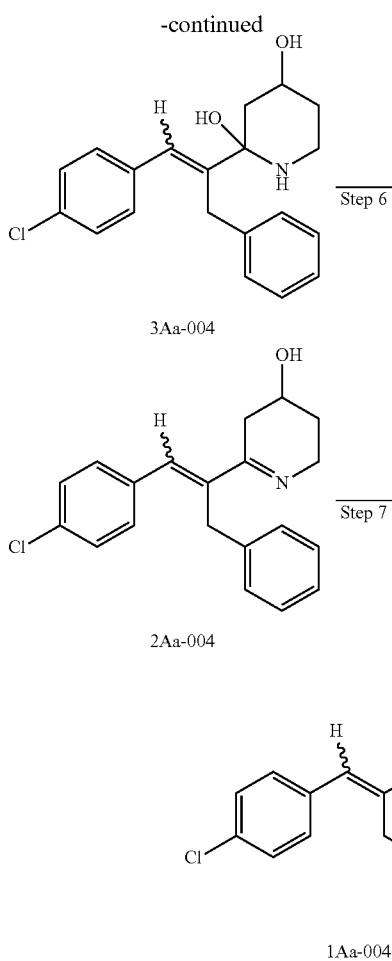

3Aa-004

2Aa-004

1Aa-004

(Step 1)
In the same manner as in Example 1, Step 1, and by using aldehyde 9a-04 and hydroxylamine hydrochloride as substrates, oxime 8a-04 was obtained as a colorless solid (yield 87%).

(Step 2)
In the same manner as in Example 1, Step 2, and by using oxime 8a-04 and N-Boc-aminobutene 7A-01 as substrates, dihydroisoxazole 6Aa-04 was obtained as colorless liquid (yield 62%).

$^1$H NMR (300 MHz, CDCl$_3$): δ1.43 (s, 9H), 2.44-2.80 (m, 2H), 3.12-3.40 (m, 4H), 3.94 (s, 2H), 4.62-4.76 (m, 1H), 5.10-5.18 (br, 1H), 6.80 (s, 1H), 7.12-7.56 (m, 9H).

(Step 3)
In the same manner as in Example 1, Step 3, and by using dihydroisoxazole 6Aa-04 as a substrate, N-Boc aminohydroxyketone 5Aa-004 was obtained as colorless liquid (yield 65%).

$^1$H NMR (300 MHz, CDCl$_3$): δ1.43 (s, 9H), 2.46-2.84 (m, 2H), 3.14-3.42 (m, 4H), 3.95 (s, 2H), 4.14-4.22 (m, 1H), 5.12-5.20 (br, 1H), 7.10-7.60 (m, 10H).

(Steps 4 and 5)
In the same manner as in Example 1, Steps 4 and 5, and by using N-Boc aminohydroxyketone 5Aa-004 as a substrate, a mixture of aminohydroxyketone 4Aa-004 and cyclic hemiaminal 3Aa-004 was obtained as yellow liquid (yield 80%).

$^1$H NMR (300 MHz, CDCl$_3$): δ2.46-2.84 (m, 2H), 3.12-3.42 (m, 4H), 3.94 (s, 2H), 4.08-4.20 (m, 1H), 6.20 (s, 1H), 7.12-7.60 (m, 9H).

(Steps 6 and 7)
In the same manner as in Example 1, Step 6, and by using a mixture of aminohydroxyketone 4Aa-004 and cyclic hemiaminal 3Aa-004 as a substrate, cyclic imine 2Aa-004 was obtained. In the same manner as in Example 1, Step 7, bicyclic oxaziridine 1Aa-004 was obtained as yellow liquid (yield 15%).

MS: m/z 342 ([M+1], C$_{20}$H$_{20}$ClNO$_2$)

INDUSTRIAL APPLICABILITY

According to the present invention, a production method of kakeromycin and a derivative thereof showing an antifungal activity and cytotoxicity and expected as a new antifungal agent or anticancer agent, by chemical synthesis is provided.

This application is based on patent application No. 2015-039363 filed in Japan, the contents of which are encompassed in full herein.

The invention claimed is:

1. A compound represented by the formula (2):

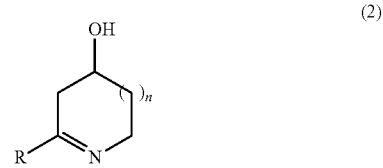

(2)

wherein
R is al a group represented by formula (A):

(A)

wherein R$^1$ and R$^2$ are the same or different and each is an optionally substituted hydrocarbon group or an optionally substituted heterocyclic group, (2) an optionally substituted C$_{1-20}$ alkyl group, (3) an optionally substituted C$_{6-20}$ aryl group, or (4) an optionally substituted C$_{7-20}$ aralkyl group, and
n is 1,
or a salt thereof.

2. The compound of claim 1, wherein R is a group represented by formula (A):

(A)

wherein r$^1$ and R$^2$ are the same or different and each is an optionally substituted hydrocarbon group or an optionally substituted heterocyclic group, or a salt thereof.

3. The compound of claim 2, wherein R$^1$ and R$^2$ are the same or different and each is an unsubstituted hydrocarbon group or an unsubstituted heterocyclic group, or a salt thereof.

4. The compound of claim 1, wherein R is an optionally substituted $C_{1-20}$ alkyl group.

5. The compound of claim 1, wherein R is an optionally substituted $C_{6-20}$ aryl group.

6. The compound of claim 1, wherein R is an optionally substituted $C_{7-20}$ aralkyl group.

7. The compound of claim 1, wherein R is an unsubstituted $C_{1-20}$ alkyl group.

8. The compound of claim 1, wherein R is an unsubstituted $C_{6-20}$ aryl group.

9. The compound of claim 1, wherein R is an unsubstituted $C_{7-20}$ aralkyl group.

* * * * *